US00PP08627P

United States Patent [19]

de Ruiter

[11] Patent Number: Plant 8,627

[45] Date of Patent: Mar. 8, 1994

[54] MINIATURE ROSE PLANT NAMED RUIHONZEV

[75] Inventor: Gijsbert de Ruiter, Voorweg, Netherlands

[73] Assignee: De Ruiter's Nieuwe Rozen B.V., Hazerswoude, Netherlands

[21] Appl. No.: 999,225

[22] Filed: Dec. 31, 1992

[51] Int. Cl.[5] ..... A01H 5/00

[52] U.S. Cl. ..... Plt./9

[58] Field of Search ..... Plt. 7.1, 9, 10

*Primary Examiner*—Howard J. Locker

*Attorney, Agent, or Firm*—Christie, Parker & Hale

[57] ABSTRACT

A new variety of miniature rose plant having light and medium pink flowers produced on a good pot-forcing plant.

2 Drawing Sheets

SUMMARY OF THE INVENTION

The present invention relates to a new and distinct variety of rose plant of the miniature rose class, which was originated by me by crossing as the seed and pollen parents unnamed and unpatented seedlings of my creation. The varietal denomination of the new variety is 'Ruihonzev'.

Among the novel characteristics possessed by this new variety which distinguishes it from its parents and all other varieties of which I am aware are its light and medium pink flowers borne on a plant particularly suited for production of flowering pot plants. The new variety can be reproduced through propagation by cuttings, grafting, budding, and micropropagation. Flowers of the new variety are long lasting on the plant. Asexual reproduction by budding, grafting and propagation of cuttings of the new variety as performed in Hazerswoude, Holland, shows that the foregoing and other distinguishing characteristics come true to form and are established and transmitted through succeeding propagations.

BRIEF DESCRIPTION OF ILLUSTRATIONS

The accompanying illustrations show typical specimens of the vegetative growth and flowers of the new variety in different stages of development depicted in color as nearly true as it is reasonably possible to make the same in a color illustration of this character. Phenotypic expression, including colors, may vary depending upon growing conditions, such as under different climate, soil, and cultivation conditions.

One accompanying illustration is of a plant of the new variety of miniature rose showing flowering and growth habit; but the colors depicted are not true because of bright light reflection on the flowers. The other illustration shows details of the new miniature rose variety illustrated in colors believed to more accurately depict flower coloration.

DETAILED DESCRIPTION OF THE NEW VARIETY

Figure 1:
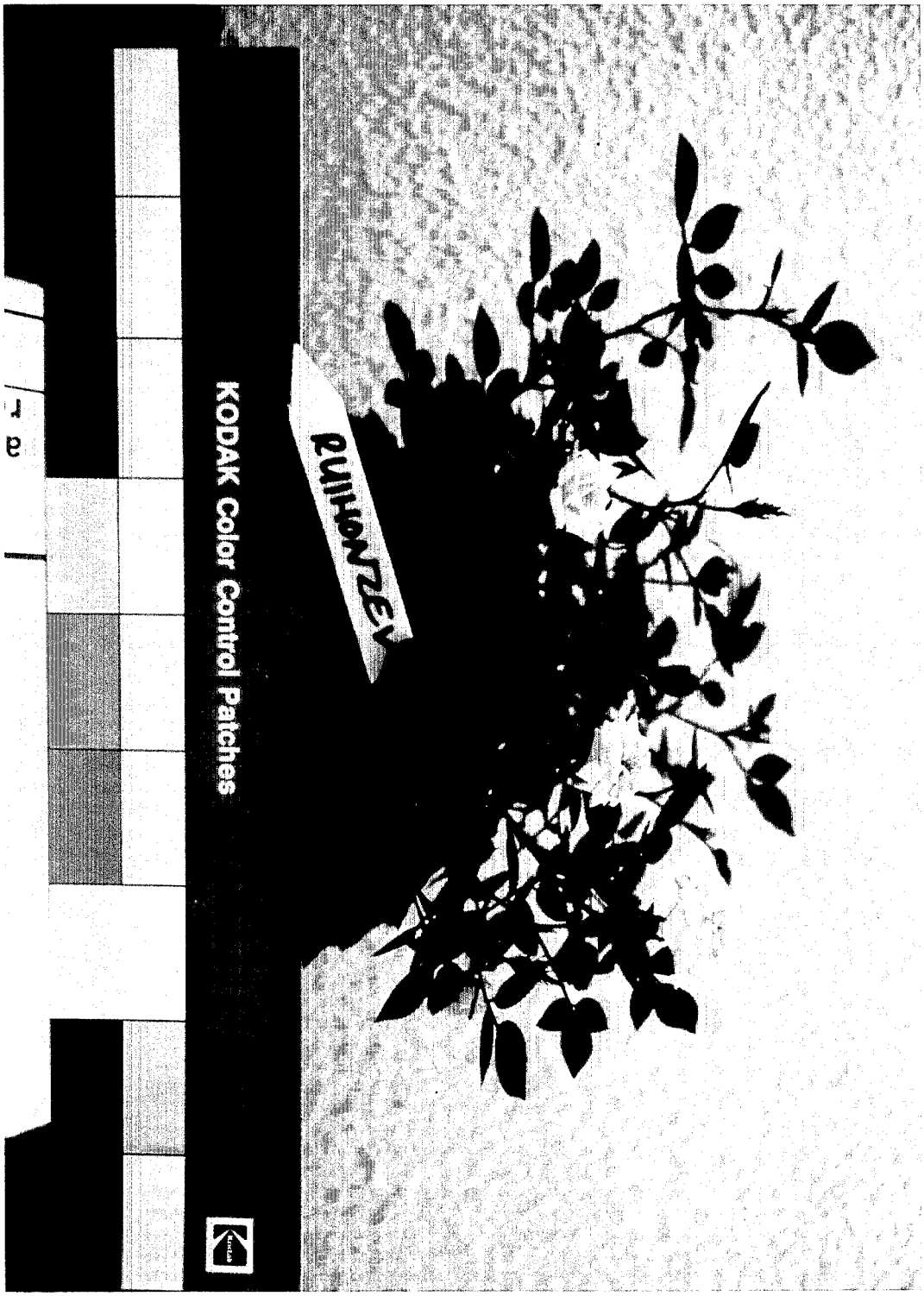

The following is a detailed description of my new variety, with color terminology in accordance with The Royal Horticultural Society Colour Chart (R.H.S.C.C.) and horticultural terminology in accordance with standard terminology used in UPOV-approved horticultural guidelines. The terminology used in color descriptions herein refers to plate numbers in the aforementioned color chart.

Parentage: Seedling.

*Seed parent.*—Unnamed seedling.

*Pollen parent.*—Unnamed seedling.

Class: Miniature.

As can be seen in the accompanying illustrations, one illustration shows one sample of flowering plant of the new variety depicting the pot plant habit of growth and flowering. Since flowering is nearly continuous, this floriferous variety can remain attractively in bloom for long periods when given proper care and culture.

The other illustration shows details of the new variety. In the illustration there is shown the top of a young shoot, 1; compound three and five leaflet leaves, 2, and 3, respectively; a stem, 5; buds, 6 and 7; a flower, 8, about one-half open; and a flower 9, fully open. Also shown are portions of flower stems 10, 11 and 12, with reproductive organs.

The following further horticultural observations were made of specimens grown under glass in Holland.

Flower

Blooming habit: Nearly continuous.

A. Bud:

(1) *Size.*—Small.

(2) *Form.*—Ovate (before separation of sepals); broad ovoid after sepals part.

(3) *Color.*—As sepals divide, bud color is near 55D.

(4) *Sepals.*—About same length as bud, simple to foliated.

(5) *Peduncle.*—Length — short to medium for miniature. Aspect — straight. Strength — erect. Color — medium green.

B. Bloom:

*Flower.*—Medium size for miniature; view from above — round; viewed from side, (a) upper part of fully opened flower, flattened convex; (b) lower part of fully opened flower, concave.

(1) *Size.*—Average size when fully expanded — about 4 cm.

(2) *Borne.*—Primarily singly, one to a stem (3) *Form.*—Broad ovoid becoming flat; outer petals quill to points, inner petals roll under.

(4) *Petalage.*—Many-petaled under normal conditions — semi-double.

(5) *Color.*—After sepals separate and part and petals being to unfurl, color is near 55D; outer petals' top surface is near 55C to 55D and inner petals tend to be deeper-toned, near 55B at center where petals bunch; reverse surface tends to be similar to top surface, but can be a little lighter. Coloring at point of petal attachment is near 29C. Overall tonality from a distance is two-toned pink. Flower coloring lightens slightly upon aging.

(6) *Pedicel.*—Very few hairs or prickles.

(7) *Fragrance.*—Slight.

C. Petals:

(1) *Texture.*—Very good substance.

(2) *Appearance.*—Inside velvety and outside satiny.

(3) *Form and size.*—Small for miniature, obovate.

(4) *Arrangement.*—Regularly arranged, imbricated.

(5) *Petaloids in center.*—Few.

(6) *Lasting quality.*—Long lasting quality on plant.

(7) *Petalage.*—About 15.

Reproductive Organs

A. Stamens, filaments and anthers:

*Arrangement and color.*—Regualrly arranged around styles; color filaments — brown to brownish yellow.

B. Pollen:

*Color.*—Orange yellow.

C. Styles: Short, white, generally not hairy.

D. Stigmas: Positioned above anthers.

E. Hips: Very small, pitcher-shaped.

Plant

A. Form: Upright, bushy, about 25 cm in height.

B. Growth: Vigorous but low-growing.

C. Foliage: Compound 3 and 5 leaflets.

(1) *Size.*—Medium to small for a miniature.

(2) *Quantity.*—Abundant.

(3) *Color.*—Foliage at time of first flowering — lgiht to medium green, slight reddening at margin of new foliage, mature foliage — near 137A.

(4) *Shape.*—Oval, pointed.

(5) *Texture.*—Upper side is weakly glossy; underside is matte.

(6) *Edge.*—Serrate.

(7) *Serration.*—Ordinary, acuminate apices.

(8) *Leaf stem.*—Color — medium green.

(9) *Stipules.*—Ordinary, long, medium to dark green, distinct auricle, foliated.

(10) *Leaflets.*—Cross section — slightly concave, little or no undulation at margin; terminal leaflet (blade) — very short, very narrow, obtuse base; petiole — medium, very few hairs on pedicel.

D. Wood:

(1) *New wood.*—Color — light to medium green, little or no anthocyanin coloration.

(2) *Old wood.*—Color — medium green.

E. Prickles (thorns):

(1) *Prickles.*—Present, quantity (main stalk) — ordinary; On laterals from stalk — ordinary; Form — straight, needle-like; Shape of upper side — flat; Shape of lower side — flat; Color — tan to pale pink; Position — irregular.

I claim:

1. A new and distinct variety of rose plant of the miniature rose class, substantially, as shown and described.

* * * * *

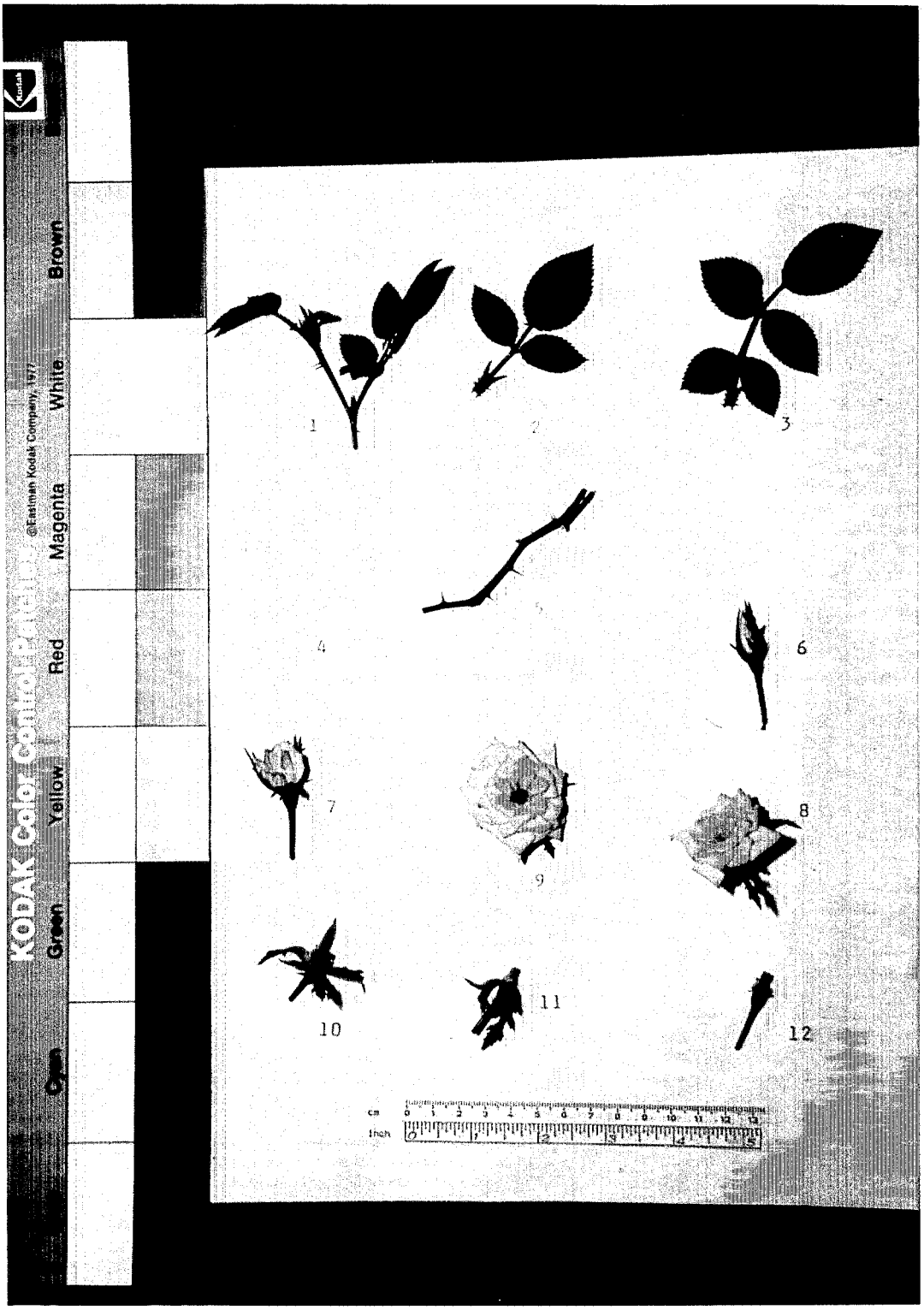
KODAK Color Control Patches
©Eastman Kodak Company, 1977
Cyan
Green
Yellow
Red
Magenta
White
Brown
1
2
3
4
5
6
7
8
9
10
11
12
cm
inch